US012557995B2

(12) United States Patent
　　Kang et al.

(10) Patent No.: US 12,557,995 B2
(45) Date of Patent: Feb. 24, 2026

(54) BIO-INFORMATION ESTIMATING APPARATUS AND BIO-INFORMATION ESTIMATING METHOD

(71) Applicant: SAMSUNG ELECTRONICS CO., LTD., Suwon-si (KR)

(72) Inventors: Jae Min Kang, Seoul (KR); Yong Joo Kwon, Yongin-si (KR); Youn Ho Kim, Hwaseong-si (KR); Sang Yun Park, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 947 days.

(21) Appl. No.: 17/500,517

(22) Filed: Oct. 13, 2021

(65) Prior Publication Data

US 2022/0031175 A1　　Feb. 3, 2022

Related U.S. Application Data

(62) Division of application No. 16/361,447, filed on Mar. 22, 2019, now Pat. No. 11,419,507.

(30) Foreign Application Priority Data

Sep. 11, 2018　(KR) ........................ 10-2018-0108500

(51) Int. Cl.
　　*A61B 5/021*　　(2006.01)
　　*A61B 5/00*　　(2006.01)
　　　　(Continued)

(52) U.S. Cl.
　　CPC ........ *A61B 5/02116* (2013.01); *A61B 5/0261* (2013.01); *A61B 5/7239* (2013.01);
　　　　(Continued)

(58) Field of Classification Search
　　CPC ........................... A61B 5/022; A61B 5/02225
　　　　(Continued)

(56) References Cited

U.S. PATENT DOCUMENTS 6,277,637 B1　8/2001　Lintilhac et al.
7,029,448 B2　4/2006　Kubo
　　　(Continued)

FOREIGN PATENT DOCUMENTS

CN　　106560155 A　　4/2017
CN　　107928643 A　　4/2018
　　　(Continued)

OTHER PUBLICATIONS

Anand Chandrasekhar et al. "Smartphone-based blood pressure monitoring via the oscillometric finger-pressing method" Science Translational Medicine, Research Article, vol. 10, No. 431, Mar. 7, 2018, (12 pages total) XP055463286.

(Continued)

*Primary Examiner* — Puya Agahi
(74) *Attorney, Agent, or Firm* — Sughrue Mion, PLLC

(57) ABSTRACT

A bio-information estimating apparatus includes a sensor part configured to measure a pulse wave signal from an object, a contact force that is applied by the object to the sensor part, and a contact area of the object that is applied to the sensor part, and a processor configured to obtain a first feature value, based on a first change in the contact area with respect to a second change in the contact force, obtain a second feature value, based on the pulse wave signal, and estimate bio-information, based on the first feature value and the second feature value.

9 Claims, 12 Drawing Sheets

(51) Int. Cl.

| | |
|---|---|
| *A61B 5/02* | (2006.01) |
| *A61B 5/022* | (2006.01) |
| *A61B 5/026* | (2006.01) |

(52) U.S. Cl.
CPC ............. *A61B 5/02* (2013.01); *A61B 5/02225* (2013.01); *A61B 5/6801* (2013.01); *A61B 5/6824* (2013.01)

(58) Field of Classification Search
USPC ......................................................... 600/481
See application file for complete search history.

(56) References Cited

U.S. PATENT DOCUMENTS

| | | | |
|---|---|---|---|
| 9,737,220 B2 | 8/2017 | Kim et al. | |
| 10,448,848 B2 | 10/2019 | Park et al. | |
| 10,813,561 B2 | 10/2020 | Kwon et al. | |
| 10,820,858 B2 | 11/2020 | Yoon et al. | |
| 11,517,211 B2 | 12/2022 | Park et al. | |
| 11,666,277 B2 | 6/2023 | Yoon et al. | |
| 2008/0087098 A1* | 4/2008 | Qu ....................... | A61B 5/0055 |
| | | | 73/849 |
| 2014/0051941 A1 | 2/2014 | Messerschmidt | |
| 2014/0076063 A1 | 3/2014 | Lisseman et al. | |
| 2014/0276149 A1 | 9/2014 | Takahashi et al. | |
| 2016/0157733 A1 | 6/2016 | Gil | |
| 2016/0196635 A1 | 7/2016 | Cho et al. | |
| 2016/0278645 A1 | 9/2016 | Yoon | |
| 2016/0278704 A1* | 9/2016 | Park ....................... | A61B 5/02 |
| 2017/0215749 A1 | 8/2017 | Zhuo et al. | |
| 2017/0251935 A1 | 9/2017 | Yuen | |
| 2018/0078154 A1 | 3/2018 | Knickerbocker et al. | |
| 2018/0132731 A1 | 5/2018 | Albadawi et al. | |
| 2018/0177413 A1* | 6/2018 | Kwon ................. | A61B 5/0053 |
| 2019/0104997 A1 | 4/2019 | Kang et al. | |
| 2019/0298251 A1 | 10/2019 | Kanaumi et al. | |

FOREIGN PATENT DOCUMENTS

| | | | |
|---|---|---|---|
| CN | 108236460 A | 7/2018 | |
| EP | 3342336 A1 | 7/2018 | |
| EP | 3469984 A1 | 4/2019 | |
| JP | 2003-284696 A | 10/2003 | |
| JP | 2009-39267 A | 2/2009 | |
| JP | 2014-147637 A | 8/2014 | |
| KR | 10-2006-0081178 A | 7/2006 | |
| KR | 10-2008-0054855 A | 6/2008 | |
| KR | 10-2010-0022614 A | 3/2010 | |
| KR | 10-1512076 B1 | 4/2015 | |
| KR | 10-2016-0115017 A | 10/2016 | |
| KR | 10-2017-0006106 A | 1/2017 | |
| KR | 10-2017-0041117 A | 4/2017 | |
| WO | 2017152098 A1 | 9/2017 | |
| WO | 2018096864 A1 | 5/2018 | |

OTHER PUBLICATIONS

Communication dated Nov. 18, 2019, from the European Patent Office in counterpart European Application No. 19173572.9.

Communication dated Sep. 15, 2020, from the European Patent Office in European Application No. 19173572.9.

J. E. de Groot et al., "A novel approach to mammographic breast compression: Improved standardization and reduced discomfort by controlling pressure instead of force", Medical Physics, Aug. 2013, vol. 40, No. 8, pp. 081901-1-081901-11 (13 pages total).

Office Action issued Mar. 2, 2023 by the Korean Intellectual Property Office in corresponding Korean Application No. 10-2018-0108500.

Communication issued Nov. 30, 2023 by the State Intellectual Property Office of People's Republic of China in Chinese Application No. 201910397278.X.

* cited by examiner

BIO-INFORMATION ESTIMATING APPARATUS AND BIO-INFORMATION ESTIMATING METHOD

CROSS-REFERENCE TO RELATED APPLICATION

This application is a divisional application of U.S. application Ser. No. 16/361,447 filed Mar. 22, 2019, which claims priority from Korean Patent Application No. 10-2018-0108500, filed on Sep. 11, 2018, in the Korean Intellectual Property Office, the disclosure of which is incorporated herein by reference in its entirety.

BACKGROUND

1. Field

Apparatuses and methods consistent with embodiments relate to a bio-information estimating apparatus and a bio-information estimating method, and more particularly to technology for cufflessly estimating blood pressure.

2. Description of Related Art

As a method of measuring blood pressure in a non-invasive manner without damaging a human body, there is a cuff-based measurement method for measuring blood pressure, using cuff pressure measurements, and a cuffless measurement method for estimating blood pressure, using pulse wave measurements without a cuff.

Options for the cuff-based measurement method for measuring blood pressure include a Korotkoff-sound method that measures blood pressure by winding a cuff around an upper arm and hearing the sound of blood vessels through a stethoscope during inflation and deflation of the cuff; and an Oscillometric method that measures blood pressure by winding a cuff around an upper arm, continuously measuring cuff pressure while inflating and then gradually deflating the cuff using an automated device, and measuring blood pressure based on a point of maximum pressure signal change.

Options for the cuffless measurement method for measuring blood pressure include a method of estimating blood pressure by calculating a Pulse Transit Time (PTT), and a Pulse Wave Analysis (PWA) method of estimating blood pressure by analyzing a pulse wave form.

SUMMARY

According to embodiments, there is provided a bio-information estimating apparatus including a sensor part configured to measure a pulse wave signal from an object, a contact force that is applied by the object to the sensor part, and a contact area of the object that is applied to the sensor part, and a processor configured to obtain a first feature value, based on a first change in the contact area with respect to a second change in the contact force, obtain a second feature value, based on the pulse wave signal, and estimate bio-information, based on the first feature value and the second feature value.

The sensor part may include a pulse wave sensor including a light source configured to emit first light onto the object, and a detector configured to detect second light that is reflected from the object, and a contact pressure sensor including a force sensor configured to measure the contact force, and an area sensor configured to measure the contact area.

The processor may be further configured to create a contact area change graph representing the first change in the contact area with respect to the second change in the contact force, by plotting the contact area with respect to the contact force at each of measurement time points, and obtain the first feature value, using the contact area change graph.

The processor may be further configured to perform fitting on the contact area change graph, perform differentiation on the contact area change graph on which the fitting is performed, and obtain the first feature value, based on the contact area change graph on which the differentiation is performed.

The first feature value may include any one or any combination of a maximum slope, a minimum slope, and an average slope of each of predetermined unit sections of the contact area change graph.

The processor may be further configured to obtain a contact pressure between the object and the sensor part, based on the contact force and the contact area, and obtain the second feature value, based on the contact pressure and the pulse wave signal.

The processor may be further configured to obtain an oscillometric envelope representing the contact pressure versus the pulse wave signal at each of the measurement time points, and obtain the second feature value, based on the oscillometric envelope.

The second feature value may include any one or any combination of a maximum amplitude value of the oscillometric envelope, a first contact pressure value corresponding to the maximum amplitude value, a plurality of contact pressure values that are located to a left and a right of the first contact pressure value and have a predetermined ratio to the first contact pressure value, and a plurality of amplitude values of the oscillometric envelope that corresponds to the plurality of contact pressure values.

The sensor part is further configured to measure a plurality of pulse wave signals from the object, and the processor may be further configured to obtain a plurality of oscillometric envelopes, based on the plurality of pulse wave signals and the contact pressure, obtain a plurality of feature values, based on the plurality of oscillometric envelopes, and obtain the second feature value by combining the plurality of feature values.

The bio-information estimating apparatus may further include an output interface configured to receive a request for estimating the bio-information, and output guide information of a contact pressure between the object and the sensor part.

The guide information may be for inducing a user to gradually increase the contact pressure that is applied by the object to the sensor part, or to gradually decrease the contact pressure when the user touches the sensor part with a pressure intensity greater than or equal to a predetermined threshold.

The processor may be further configured to obtain a contact pressure between the object and the sensor part, based on the contact force and the contact area, and determine a contact state between the object and the sensor part, based on the contact pressure.

The processor may be further configured to determine whether the contact state is normal, and the apparatus may further include an output interface configured to, based on the contact state being determined to be not normal, output guide information for inducing a user to change the contact pressure.

The bio-information may include any one or any combination of a blood pressure, a vascular age, an arterial stiffness, an aortic pressure waveform, a vascular compliance, a stress index, and a degree of fatigue.

According to embodiments, there is provided a bio-information estimating method being performed by a bio-information estimating apparatus, the method including measuring a pulse wave signal from an object, a contact force that is applied by the object to a sensor part of the bio-information estimating apparatus, and a contact area of the object that is applied to the sensor part, obtaining a first feature value, based on a first change in the contact area with respect to a second change in the contact force, obtaining a second feature value, based on the pulse wave signal, and estimating bio-information, based on the first feature value and the second feature value.

The obtaining of the first feature value may include creating a contact area change graph representing the first change in the contact area with respect to the second change in the contact force, by plotting the contact area with respect to the contact force at each of measurement time points, and obtaining the first feature value, using the contact area change graph.

The bio-information estimating method may further include performing fitting on the contact area change graph, and performing differentiation on the contact area change graph on which the fitting is performed, and the obtaining of the first feature value may further include obtaining the first feature value, based on the contact area change graph on which the differentiation is performed.

The first feature value may include any one or any combination of a maximum slope, a minimum slope, and an average slope of each of predetermined unit sections of the contact area change graph.

The obtaining of the second feature value may include obtaining a contact pressure between the object and the sensor part, based on the contact force and the contact area, and obtaining the second feature value, based on the contact pressure and the pulse wave signal.

The bio-information estimating method may further include obtaining an oscillometric envelope representing the contact pressure versus the pulse wave signal at each of the measurement time points, and the obtaining of the second feature value may further include obtaining the second feature value, based on the oscillometric envelope.

The second feature value may include any one or any combination of a maximum amplitude value of the oscillometric envelope, a first contact pressure value corresponding to the maximum amplitude value, a plurality of contact pressure values that are located to a left and a right of the first contact pressure value and have a predetermined ratio to the first contact pressure value, and a plurality of amplitude values of the oscillometric envelope that corresponds to the plurality of contact pressure values.

The bio-information estimating method may further include outputting an estimation result of the bio-information.

According to embodiments, there is provided a bio-information estimating apparatus including a sensor part configured to measure a contact force that is applied by an object to the sensor part, and a contact area of the object that is applied to the sensor part, and a processor configured to obtain a first feature value, based on a first change in the contact area with respect to a second change in the contact force, and estimate first bio-information, based on the first feature value.

The processor may be further configured to create a contact area change graph representing the first change in the contact area with respect to the second change in the contact force, by plotting the contact area with respect to the contact force at each of measurement time points, and obtain the first feature value, using the contact area change graph.

The first feature value may include any one or any combination of a maximum slope, a minimum slope, and an average slope of each of predetermined unit sections of the contact area change graph.

The first bio-information may include either one or both of skin elasticity and skin age.

As a change trend of the first feature value increases in comparison to a reference feature value that is obtained from a user at a reference time, the skin elasticity may decrease, and the skin age may increase, and as the change trend of the first feature value decreases compared to the reference feature value, the skin elasticity may increase, and the skin age may decrease.

The processor may be further configured to estimate either one or both of the skin elasticity and the skin age by applying a pre-defined bio-information estimation model to a change trend of the first feature value in comparison with a plurality of feature values that is obtained from a plurality of subjects.

The sensor part may be further configured to measure a pulse wave signal, and the processor may be further configured to obtain a second feature value, based on the pulse wave signal, and estimate second bio-information, based on the first feature value and the second feature value.

The second bio-information may include a blood pressure, and the processor may be further configured to obtain an oscillometry of the pulse wave signal, and obtain the second feature value, based on the oscillometry.

The bio-information estimating apparatus may further include an output interface configured to output an estimation result of the first bio-information and the second bio-information.

The bio-information estimating apparatus may further include a communication interface configured to transmit an estimation result of the first bio-information and the second bio-information, to an external device.

According to embodiments, there is provided a wearable device including a main body, a strap, a sensor part disposed in the main body, and configured to measure a pulse wave signal from an object, a contact force that is applied by the object to the sensor part, and a contact area of the object that is applied to the sensor part, and a processor configured to obtain a first feature value of a contact area change graph representing a first change in the contact area with respect to a second change in the contact force, obtain a contact pressure between the object and the sensor part, based on the contact force and the contact area, obtain an oscillometric envelope representing the contact pressure versus the pulse wave signal, obtain a second feature value of the oscillometric envelope, and estimate bio-information, based on the first feature value and the second feature value.

The first feature value may include any one or any combination of a maximum slope, a minimum slope, and an average slope of the contact area change graph, the second feature value may include any one or any combination of a maximum amplitude value of the oscillometric envelope, a first contact pressure value corresponding to the maximum amplitude value, a plurality of contact pressure values that are located to a left and a right of the first contact pressure value and have a predetermined ratio to the first contact pressure value, and a plurality of amplitude values of the oscillometric envelope that corresponds to the plurality of contact pressure values, and the bio-information may include any one or any combination of a blood pressure, a vascular age, an arterial stiffness, an aortic pressure wave-form, a vascular compliance, a stress index, and a degree of fatigue.

DETAILED DESCRIPTION OF EMBODIMENTS

Figure 1A:
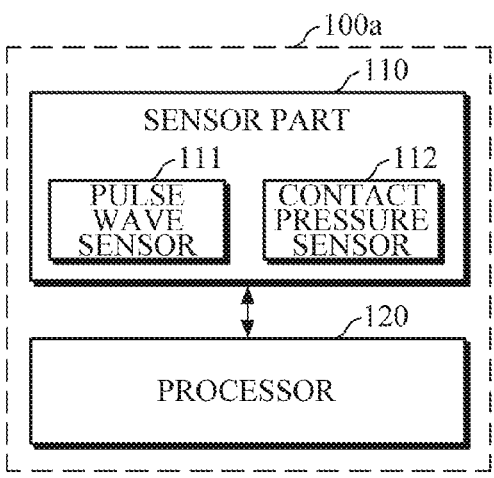
FIGS. 1A and 1B are block diagrams illustrating a bio-information estimating apparatus according to embodiments.

Details of other embodiments are included in the follow-ing detailed description and drawings. Advantages and fea-tures of the embodiments, and a method of achieving the same will be more clearly understood from the following embodiments described in detail with reference to the accompanying drawings. Throughout the drawings and the detailed description, unless otherwise described, the same drawing reference numerals will be understood to refer to the same elements, features, and structures.

It will be understood that, although the terms first, second, etc. may be used herein to describe various elements, these elements may not be limited by these terms. These terms are only used to distinguish one element from another. Any references to singular may include plural unless expressly stated otherwise. In addition, unless explicitly described to the contrary, an expression such as "comprising" or "includ-ing" will be understood to imply the inclusion of stated elements but not the exclusion of any other elements. Also, the terms, such as 'part' or 'module', etc., may be under-stood as a unit that performs at least one function or operation and that may be embodied as hardware, software, or a combination thereof.

Hereinafter, embodiments of a bio-information estimating apparatus and a bio-information estimating method will be described in detail with reference to the accompanying drawings.

Figure 1B:
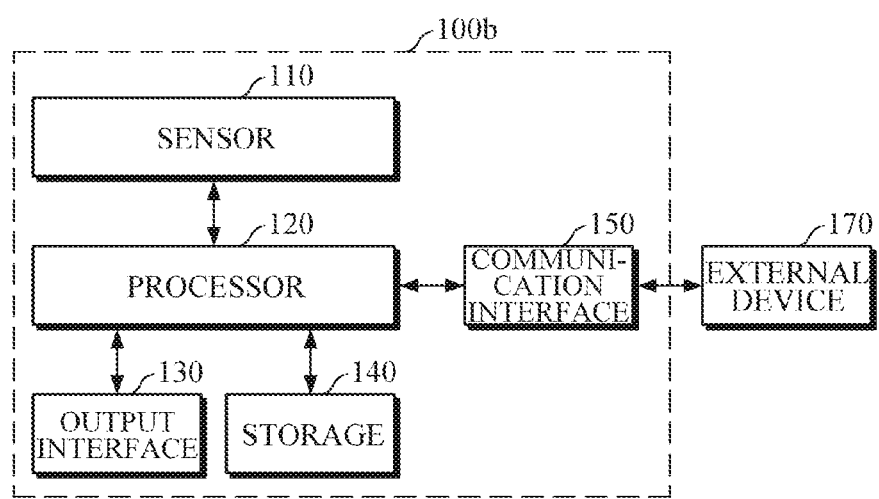

FIGS. 1A and 1B are block diagrams illustrating a bio-information estimating apparatus according to embodi-ments. Various embodiments of bio-information estimating apparatuses 100a and 100b may be embedded in various devices, such as a portable wearable device, a smart device, and the like. Examples of the various devices may include, but are not limited to, a wearable device of various types such as a smart watch worn on the wrist, a smart band-type wearable device, a headphone-type wearable device, a hair-band-type wearable device, and the like, a mobile device such as a smartphone, a tablet PC, and the like. Examples of bio-information that may be estimated by the bio-information estimating apparatus may include heart rate, blood pressure, vascular age, arterial stiffness, aortic pressure waveform, vascular compliance, stress index, degree of fatigue, skin elasticity, skin age, and the like, but is not limited thereto. For convenience of explanation, the follow-ing description will be made using blood pressure, skin elasticity, and skin age as an example.

Referring to FIG. 1A, the bio-information measuring apparatus 100 includes a sensor part 110 and a processor 120.

The sensor part 110 may include a pulse wave sensor 111 to measure pulse wave signals, including a photoplethys-mography (PPG) signal, from an object to estimate bio-information. The pulse wave sensor 111 may include: a light source that emits first light onto an object; and a detector that detects second light emitted by the light source and scattered or reflected from the living body tissue, such as the skin surface, blood vessel, and the like of the object.

The light source may include a light emitting diode (LED), a laser diode (LD), a fluorescent body, and the like, but is not limited thereto. Further, the detector may include one or more pixels, each of which may include a photo diode, a photo transistor (PTr), an image sensor (e.g., CMOS image sensor), and the like, but is not limited thereto. In addition, the pulse wave sensor 111 may include an array of a plurality of light sources and/or an array of a plurality of detectors to measure two or more pulse wave signals. In this case, the plurality of light sources may emit light of different wavelengths. Each of the light sources may be disposed at different distances from the detector.

Further, the sensor part 110 may include a contact pres-sure sensor 112, and may measure a contact force, which is applied by an object to the sensor part 110 when the object touches the sensor part 110 to measure a pulse wave signal, and a contact area. The contact pressure sensor 112 may include a force sensor for measuring a contact force applied by an object to the sensor part 11, and an area sensor for measuring a contact area between the object and the sensor part 110 according to a change in the contact force applied by the object to the sensor part 110. However, examples of the sensors are not limited thereto.

The processor 120 may be electrically connected to the sensor part 110. In response to receiving a request for estimating bio-information from a user, or predetermined criteria for estimating bio-information being satisfied, the processor 120 may control the sensor part 110, and may receive a pulse wave signal, and/or a contact force and a contact area from the sensor part 110.

The processor 120 may estimate bio-information based on the received pulse wave signal, contact force, and contact area.

In one embodiment, the processor 120 may estimate blood pressure by using the received pulse wave signal, contact force, and contact area. The processor 120 may extract feature values based on the pulse wave signal, and may estimate blood pressure using oscillometry using the extracted feature values. For example, as the contact pres-sure between an object and the sensor part 110 changes, the amplitude of the pulse wave signal shows an increasing/decreasing pattern. By using feature values associated with the increase/decrease in the amplitude of the pulse wave signal, the processor 120 may estimate blood pressure. In this case, the processor 120 may additionally obtain feature values that represent a first change in a contact area with respect to a second change in a contact force applied by an object to the sensor part 110 for a predetermined period of time when a pulse wave signal is measured, and may reflect the additionally obtained feature values in estimation of blood pressure using oscillometry, thereby improving the accuracy in estimating blood pressure.

In another embodiment, the processor 120 may estimate skin elasticity and/or skin age based on the contact force and the contact area. For example, the processor 120 may obtain feature values that represent a change in the contact area with respect to a change in the contact force during a predetermined period of time, and may estimate skin elasticity and/or skin age based on the obtained feature values. In embodiments, the pulse wave sensor may not be included in the sensor part 110.

In yet another embodiment, the aforementioned embodiments may be combined, i.e., estimation of blood pressure using the pulse wave signal, the contact force, and the contact area, may be performed along with estimation of skin elasticity and/or skin age using the contact force and the contact area.

Referring to FIG. 1B, a bio-information estimating apparatus 100*b* according to another embodiment may further include an output interface 130, a storage 140, and a communication interface 150, in addition to the sensor part 110 and the processor 120. The sensor part 110 and the processor 120 are described above with reference to FIG. 1A, such that the following description will be made based on parts that do not overlap with those.

Upon receiving a request for estimating bio-information, the processor 120 may generate guide information by referring to a reference contact pressure value of the storage 140. Further, once a contact force and a contact area are measured while the sensor part 110 measures an actual pulse wave signal, the processor 120 may calculate a contact pressure value, which is actually applied by an object, based on the measured contact force and contact area, and may generate guide information including the calculated actual contact pressure value.

In this case, the guide information may include information for inducing a user to gradually increase contact pressure applied by an object to the sensor part 110 while the object touches the sensor part 110, or conversely, to gradually decrease contact pressure when a user touches the sensor part 110 with a pressure intensity equal to or greater than a predetermined threshold. For example, the guide information may include a graph showing a change in the reference contact pressure and/or a change in the actual contact pressure during a predetermined period of time. Alternatively, the guide information may include a reference contact pressure value and/or an actual contact pressure value of a time point during a measurement period.

The output interface 130 may output processing results of the sensor part 110 and the processor 120. For example, the output interface 130 may visually output an estimated bio-information value and/or guide information by using a display module, or may output the information in a non-visual manner through voice, vibration, tactile sensation, and the like, by using a speaker module, a haptic module, and the like. A display area may be divided into two or more areas, in which the pulse wave signal, the contact force, the contact area, and the like, which are used for estimating bio-information, may be output in various forms of graphs in a first area; and an estimated bio-information value may be output in a second area. In this case, if an estimated bio-information value falls outside a normal range, the output interface 130 may output warning information in various manners, such as highlighting an abnormal value in red and the like, displaying the abnormal value along with a normal range, outputting a voice warning message, adjusting a vibration intensity, and the like.

The storage 140 may store processing results of the sensor part 110 and the processor 120. Further, the storage 140 may store various types of reference information for estimating bio-information. For example, the reference information may include user feature information such as a user's age, gender, health condition, and the like. In addition, the reference information may include various types of information, such as a bio-information estimation model, bio-information estimation criteria, a reference contact pressure value, a reference feature value, and the like, but is not limited thereto.

In this case, the storage 140 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EE-PROM), a Programmable Read Only Memory (PROM), a magnetic memory, a magnetic disk, and an optical disk, and the like, but is not limited thereto.

The communication interface 150 may communicate with an external device 170 by using wired or wireless communication techniques under the control of the processor 120, and may transmit and receive various data to and from the external device 170. For example, the communication interface 150 may transmit an estimation result of bio-information to the external device 170, and may receive various types of reference information for estimating bio-information from the external device 170. In this case, examples of the external device 170 may include a cuff-type blood pressure measuring device, and an information processing device such as a smartphone, a tablet PC, a desktop computer, a laptop computer, and the like.

In this case, examples of the communication techniques may include Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, 3G communication, 4G communication, 5G communication, and the like. However, this is an example and is not intended to be limiting.

Figure 2:
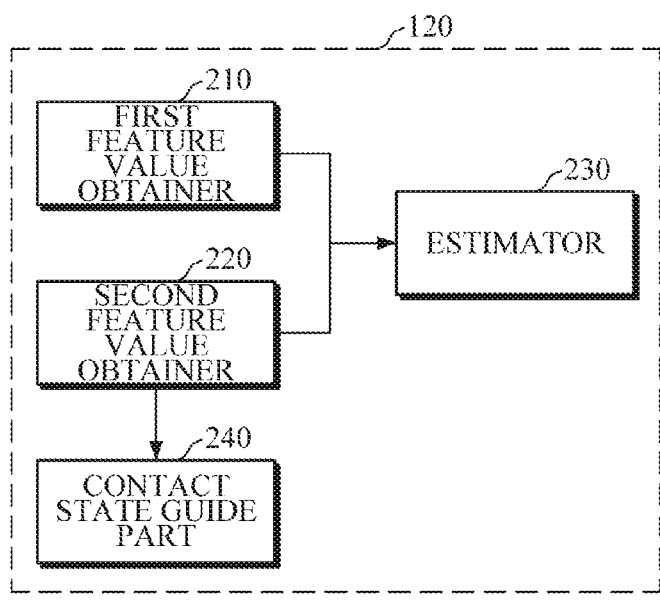
FIG. 2 is a block diagram illustrating an example of a processor of the bio-information estimating apparatuses of FIGS. 1A and 1B.
Figure 3A:
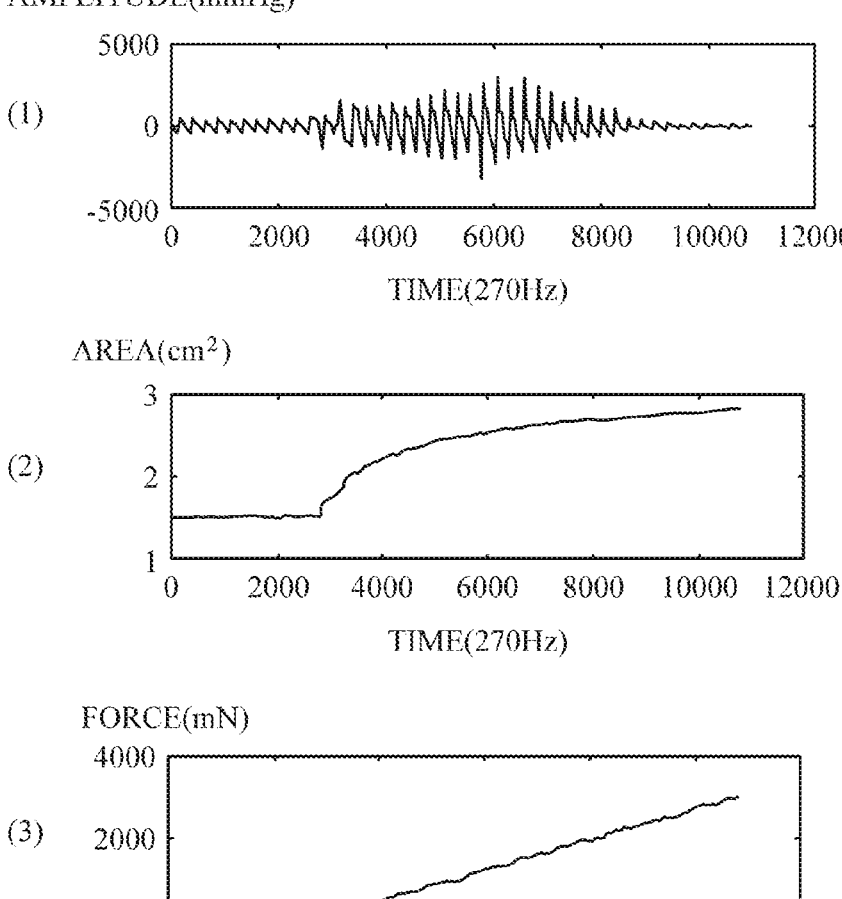
FIGS. 3A, 3B and 3C are diagrams explaining a method of obtaining a first feature value, according to embodiments.
Figure 3B:
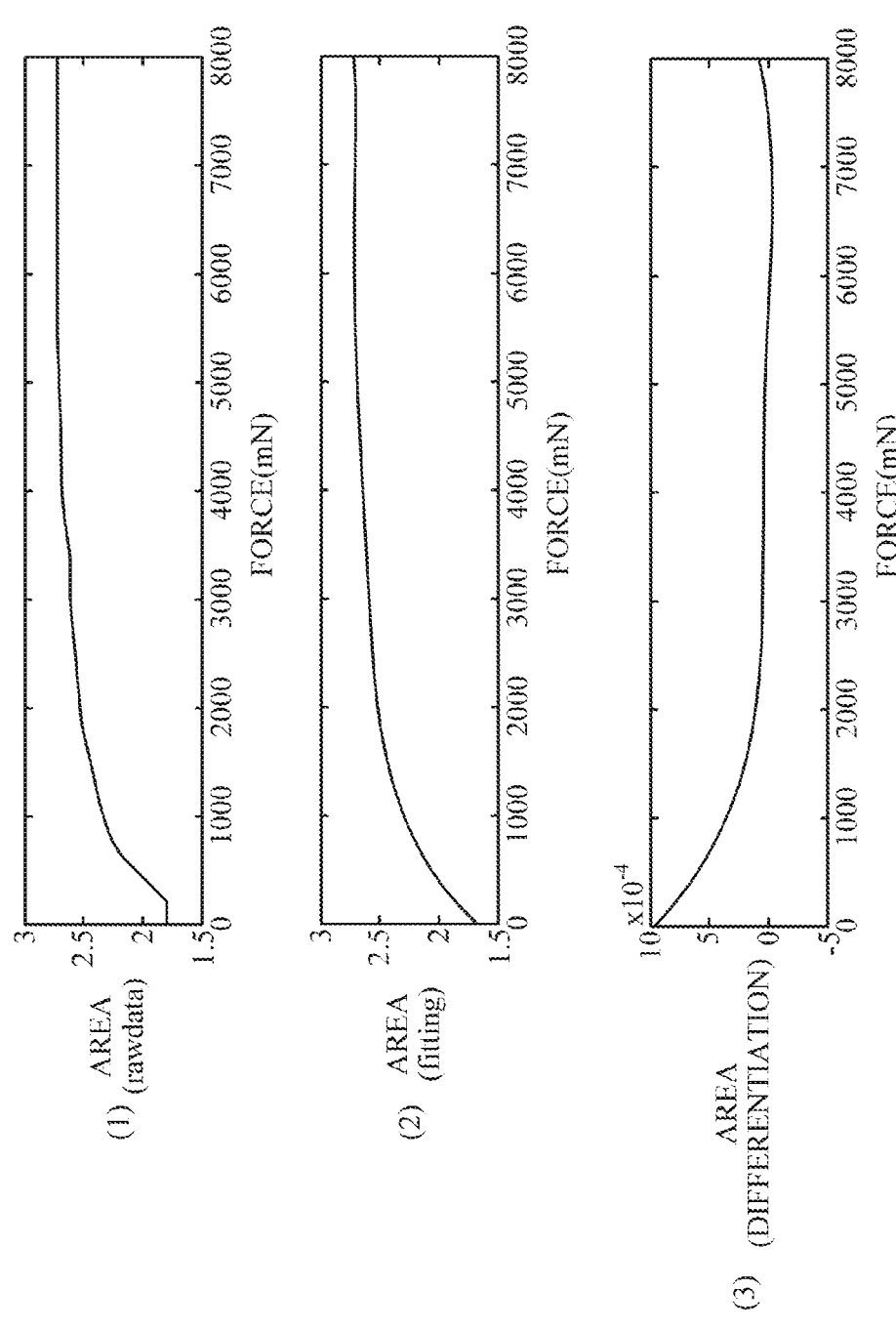
Figure 3C:
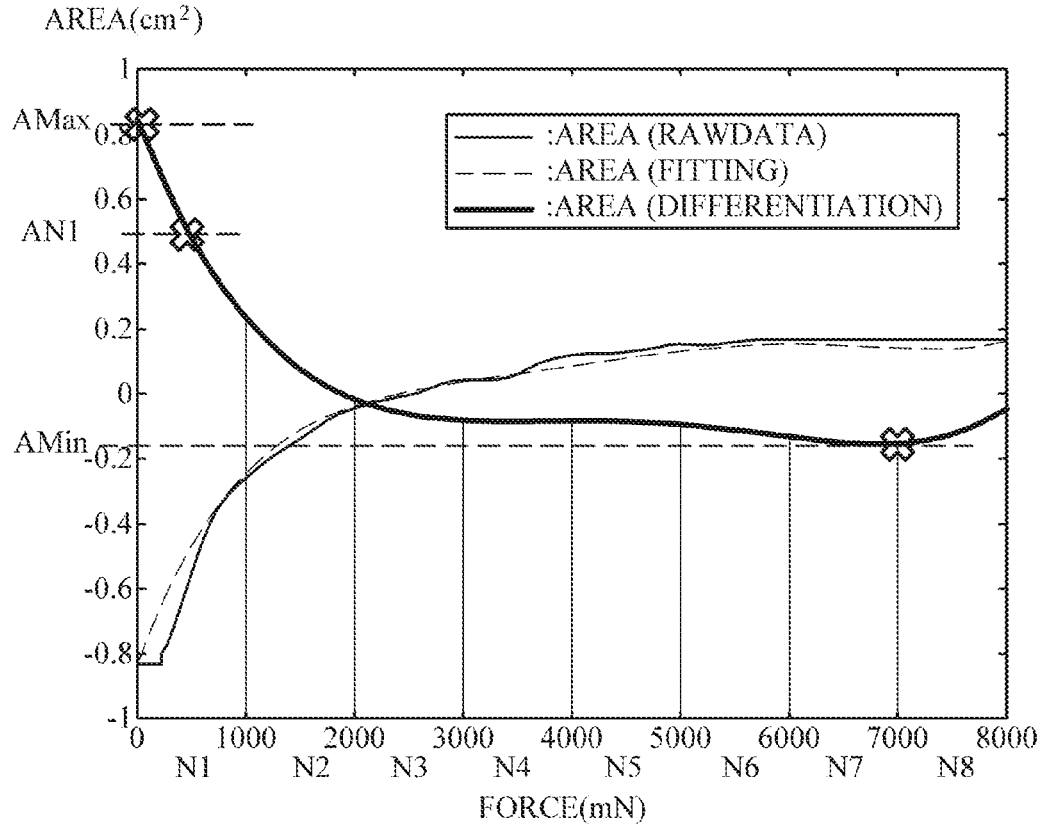
Figure 4A:
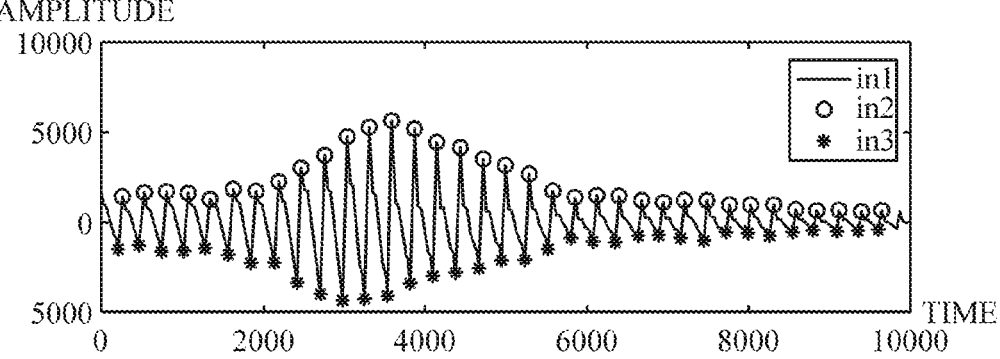
FIGS. 4A and 4B are diagrams explaining a method of obtaining a second feature value, according to embodiments.
Figure 4B:
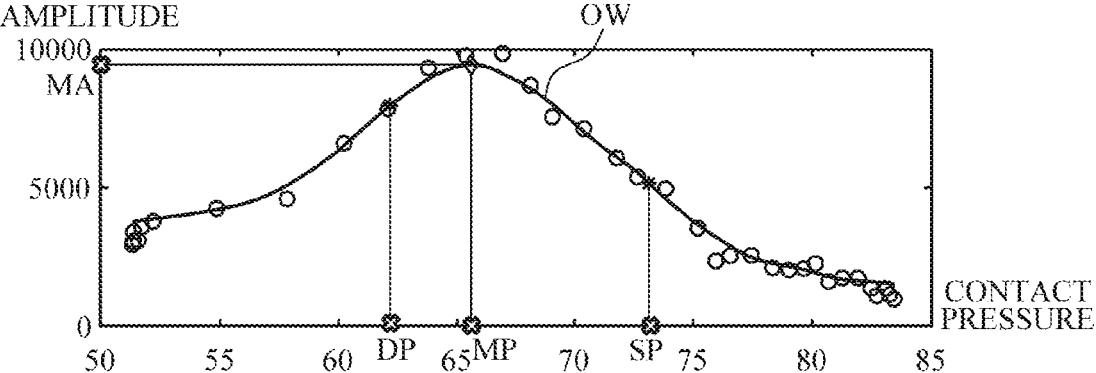
Figure 5:
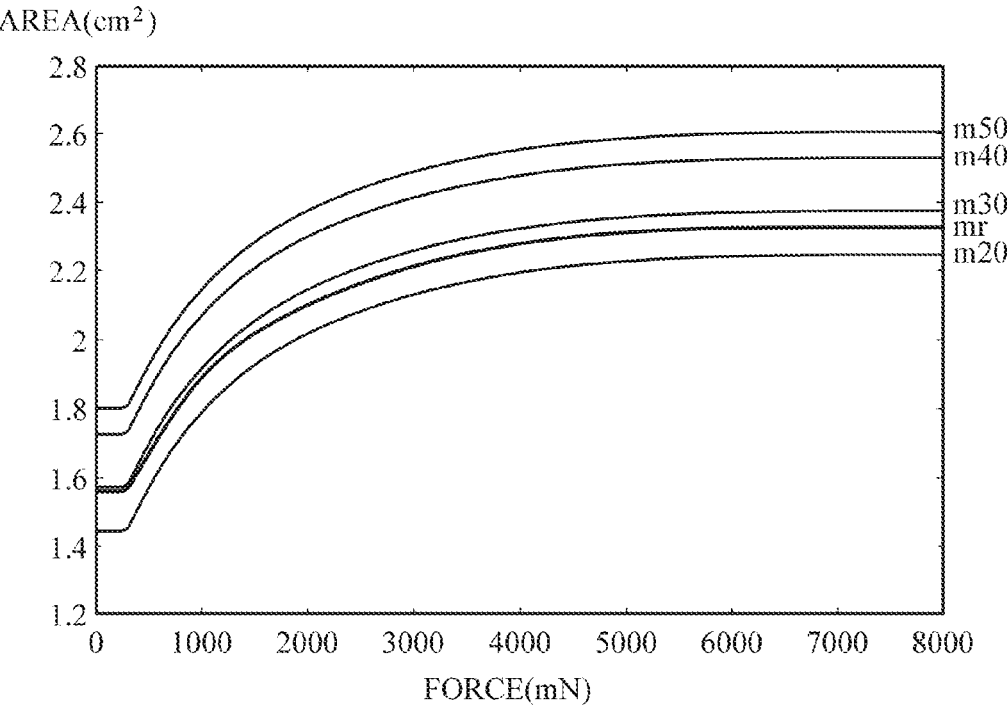
FIG. 5 is a diagram explaining a method of obtaining bio-information, according to embodiments.

FIG. 2 is a block diagram illustrating an example of the processor 120 of the bio-information estimating apparatuses 100*a* and 100*b* of FIGS. 1A and 1B. FIGS. 3A, 3B and 3C are diagrams explaining a method of obtaining a first feature value, according to embodiments. FIGS. 4A and 4B are diagrams explaining a method of obtaining a second feature value, according to embodiments. FIG. 5 is a diagram explaining a method of obtaining bio-information, according to embodiments.

Referring to FIG. 2, the processor 120 according to embodiments includes a first feature value obtainer 210, a second feature value obtainer 220, an estimator 230, and a contact state guide part 240.

FIG. 3A illustrates a pulse wave signal (1), a contact area (2), and a contact force (3), which are measured by the sensor part 110 from an object. As illustrated in FIG. 3A, when a user gradually increases force while touching the sensor part 110 with an object, a contact area increases non-linearly for a predetermined period of time, and then is saturated. The change trend of the contact area varies depending on individual characteristics such as a user's gender, age, and the like. In this case, as the contact force and the contact area between an object and the sensor part 110 changes, the amplitude of the pulse wave signal also changes.

Referring again to FIG. 2, the first feature value obtainer 210 may receive a contact force and a contact area from the sensor part 110, and based on the received contact force and contact area, the first feature value obtainer 210 may obtain a first feature value for estimating blood pressure. In this case, the first feature value may be associated with a value that represents a change in the contact area with respect to a change in the contact force during a measurement time period.

For example, referring to FIG. 3B, the first feature value obtainer 210 may create a contact area change graph, which represents a change in the contact area with respect to a change in the contact force, by plotting the contact area with respect to the contact force at each measurement time point on a time axis, as illustrated in (1). Further, upon plotting the contact area with respect to the contact force as illustrated in (1), the first feature value obtainer 210 may perform multi-dimensional equation curve fitting as illustrated in (2). In addition, the first feature value obtainer 210 may perform differentiation on the contact area change graph created in (1) or (2), and may obtain the first feature value by using the differentiated graph as illustrated in (3).

Referring to FIG. 3C, the first feature value obtainer 210 may obtain, as the first feature value, a maximum slope AMax and/or a minimum slope AMin of the contact area change graph. Further, the first feature value obtainer 210 may divide an axis of a contact force into predetermined unit sections, and may obtain an average slope of each unit section as the first feature value. FIG. 3C illustrates 8 unit sections that are divided in units of 1000 mN. As illustrated in FIG. 3C, the first feature value obtainer 210 may obtain a first average slope AN1 of a first unit section N1, and may continuously obtain an average slope of each of the unit sections in this manner. However, the first feature value is not limited thereto.

Referring again to FIG. 2, to reflect a change trend of the pulse wave amplitude according to a change in the contact force and the contact area, the second feature value obtainer 220 may obtain a second feature value based on the pulse wave signal. The second feature value obtainer 220 may obtain a contact pressure value by dividing the received contact area by the contact force, and may obtain the second feature value based on the obtained contact pressure value and the pulse wave signal.

For example, the second feature value obtainer 220 may extract a peak-to-peak point at each measurement time point of the pulse wave signal, and may obtain an oscillometric envelope, which represents contact pressure versus pulse wave, by plotting the extracted peak-to-peak point based on a contact pressure value corresponding to each measurement time point.

Referring to FIG. 4A, a pulse wave signal is obtained by gradually increasing contact pressure while a user touches the sensor part 110 with a finger or by gradually decreasing contact pressure when a user touches the sensor part 110 with a pressure intensity equal to or greater than a predetermined threshold. The second feature value obtainer 220 may extract the peak-to-peak point by subtracting an amplitude value in3 of a negative (−) point from an amplitude value in2 of a positive (+) point of the waveform envelope in1 at each measurement time point of the obtained pulse wave signal. Referring to FIG. 4B, the second feature value obtainer 220 may obtain an oscillometric envelope OW by plotting a peak-to-peak amplitude at each measurement time point based on a contact pressure value at the same measurement time point as the peak-to-peak amplitude.

Referring again to FIG. 2, the second feature value obtainer 220 may obtain one or more second feature values from the obtained oscillometric envelope OW. Referring to FIG. 4B, the second feature value obtainer 220 may obtain, as the second feature value, an amplitude value MA and a contact pressure value MP of a maximum peak point, contact pressure values SP and DP located to the left and right of the contact pressure value MP of the maximum peak point and having a predetermined ratio (e.g., 0.5 to 0.7) to the contact pressure value MP, and the like.

Referring again to FIG. 2, the sensor part 110 may measure a plurality of pulse wave signals. In this case, the second feature value obtainer 220 may select any one of the plurality of pulse wave signals, e.g., any one signal having the most significant amplitude change, and may obtain an oscillometric envelope by using the selected pulse wave signal. Alternatively, the second feature value obtainer 220 may combine two or more pulse wave signals by applying a combination model, and may obtain an oscillometric envelope by using the combined pulse wave signal. In addition, the second feature value obtainer 220 may subtract a pulse wave signal of a short wavelength from a pulse wave signal of a relatively long wavelength, and may obtain an oscillometric envelope by using a differential signal. Further, the second feature value obtainer 220 may obtain an oscillometric envelope for each of the plurality of pulse wave signals, and may obtain a second feature value by combining feature values obtained from each oscillometric envelope.

Upon obtaining the first feature value and the second feature value, the estimator 230 may estimate bio-information by combining the first feature value and the second feature value by using a pre-defined bio-information estimation model. In this case, the bio-information estimation model may be defined as various linear or non-linear combination functions, such as addition, subtraction, division, multiplication, logarithmic value, regression equation, and the like, with no specific limitation. For example, the following Equation 1 represents a simple linear equation.

$$y = af_1 + bf_2 + c \qquad \text{[Equation 1]}$$

Herein, y denotes bio-information to be obtained, e.g., systolic blood pressure (SBP), diastolic blood pressure (DBP), mean arterial pressure (MAP), and the like; $f_1$ denotes the first feature value; $f_2$ denotes the second feature value; and a, b, and c denote pre-calculated values obtained through preprocessing, and may be defined differently according to the types of bio-information to be obtained and user characteristics. Here, $f_1$ may be a value obtained by combining one or two or more of the first feature values; and likewise, $f_2$ may be a value obtained by combining one or two or more of the second feature values.

The estimator 230 may independently obtain the SBP, the DBP, and the MAP. To this end, the estimator 230 may use, for each blood pressure to be obtained, any appropriate value selected from the first feature values and/or second feature values respectively, or a value obtained by appropriately combining two or more of the first feature values and/or second feature values. For example, to obtain the MAP, the estimator 230 may substitute the contact pressure value MP of the maximum peak point of the oscillometric envelope OW, illustrated in FIG. 4B, into the second feature value $f_2$ of the above Equation 1. Further, to estimate the SBP and the DBP, the estimator 230 may substitute the contact pressure values DP and SP of points, each located to the left and right of the maximum peak point, into the second feature value $f_2$ of the above Equation 1. In this case, the plurality of first feature values obtained in FIG. 3C may be appropriately combined to be defined for each blood pressure value or may be defined as one value to be used for all the blood pressure values, and may be substituted into the first feature value $f_1$ of the above Equation 1.

In another example, the estimator 230 may estimate first bio-information, e.g., skin elasticity and/or skin age, by using the first feature values that represent a change in the contact area with respect to a change in the contact force. Further, along with the estimation of the first bio-information, the estimator 230 may estimate second bio-information, e.g., blood pressure, by using the first feature values and the second feature values as described above. In this case, it may be determined whether to estimate the first bio-information and the second bio-information concurrently or independently based on whether the sensor part 110 includes a pulse wave sensor and/or according to estimation criteria set for each user.

For example, FIG. 5 illustrates a change trend of a contact area for each age, e.g., a mean change mr for all subjects, a mean change m20 for those in their 20's, a mean change m30 for those in their 30's, a mean change m40 for those in their 40's, and a mean change m50 for those in their 50's, when a contact force is equally changed. Referring to FIG. 5, a change trend of the contact area with respect to an equal contact force is gradually increased as the age is gradually increased. This is because as the age increases, the skin elasticity decreases and the skin age increases.

Referring again to FIG. 2, the estimator 230 may estimate the skin elasticity and/or the skin age for each user by considering these skin characteristics. For example, the estimator 230 may estimate the skin elasticity and/or skin age by considering a change trend of the first feature values, obtained from a specific user, in comparison with reference feature values. In this respect, description will be made using the following examples, but the estimation is not limited thereto.

For example, the estimator 230 may estimate the skin elasticity and/or the skin age by applying a pre-defined bio-information estimation model to a change trend of the first feature values in comparison with the reference feature values obtained from the mean change of the subjects. In this case, the bio-information estimation model may be defined as various linear/non-linear combination function obtained by using a difference between the reference feature value and the first feature value as an input. However, the bio-information estimation model is not limited thereto, and may be defined as a function by using each of the reference feature value and the first feature value as an input, and may be modified various function equations through preprocessing.

In another example, the reference feature values may be obtained for various groups of subjects classified into age groups, gender groups, occupation groups, health condition groups, or a combination thereof. Upon obtaining the first feature values of a specific user, the estimator 230 may compare the obtained first feature values with the reference feature values of each group, and may estimate the skin elasticity and/or the skin age of a group, corresponding to the user, as skin elasticity and/or skin age of the user.

In yet another example, the estimator 230 may estimate that as a change trend of the first feature values, obtained from a user at a current time, increases/decreases compared to the reference feature values obtained from the same user at a reference time, the skin elasticity decreases/increases and the skin age increases/decreases.

The contact state guide part 240 may generate guide information regarding a reference contact pressure value to be applied by a user to the sensor part 110 through an object for estimating bio-information, an actual contact pressure value that is actually applied by an object to the sensor part 110, and a contact state, and may output the generated guide information through an output interface 130.

For example, upon receiving a request for estimating bio-information, the contact state guide part 240 may read a reference contact pressure value for each measurement time by referring to the storage 140, and may generate a reference contact pressure graph. Further, once the contact force and the contact area are measured at each measurement time, the contact state guide part 240 may obtain an actual contact pressure value at each measurement time, and may generate an actual contact pressure graph that represents the obtained actual contact pressure value. Further, the contact state guide part 250 may determine a contact state based on the obtained contact pressure value; and upon determination that the contact state is not normal, the contact state guide part 240 may generate information for guiding a user to change contact pressure.

Figure 6:
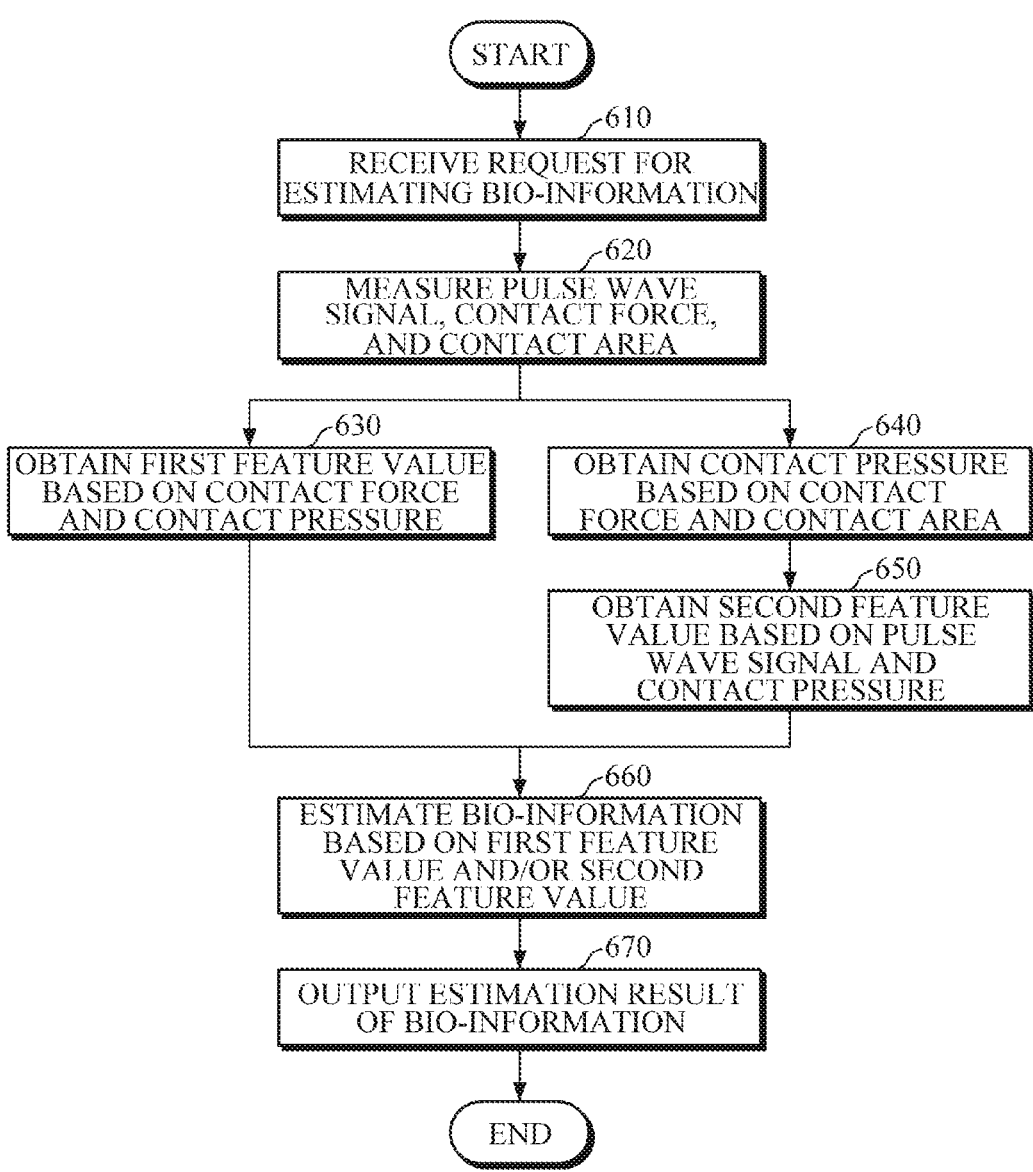
FIG. 6 is a flowchart illustrating a bio-information esti-mating method according to embodiments.

FIG. 6 is a flowchart illustrating a bio-information estimating method according to embodiments.

The bio-information measuring method of FIG. 6 may be an example of a bio-information measuring method performed by the bio-information estimating apparatuses 100a and 100b, which is described above, and thus will be described briefly to avoid redundancy.

In operation 610, the bio-information estimating apparatus may receive a request for estimating bio-information. The request for estimating bio-information may be received from a user or an external device that communicates with the bio-information estimating apparatus. However, the request for estimating bio-information is not limited thereto, and it may be determined automatically at predetermined intervals that the request for measuring bio-information is received. Upon receiving the request for measuring bio-information, the bio-information measuring apparatus may provide a user with guide information for guiding contact pressure to be applied by a user to the sensor part through an object during a predetermined period of time.

In operation 620, the bio-information estimating apparatus may measure a pulse wave signal, a contact force, and a contact area for a predetermined period of time when contact pressure changes while the object touches the sensor part. In this case, the user may change the contact pressure by gradually increasing force while touching the sensor part with a finger, or by gradually decreasing force when touching the sensor part with a finger with a pressure intensity equal to or greater than a predetermined threshold. Alternatively, the bio-information estimating apparatus may change the contact pressure by using various other methods such as touching the object from an external force.

In operation 630, the bio-information estimating apparatus may obtain first feature values based on the measured contact force and contact pressure. For example, the bio-information estimating apparatus may create a contact area change graph, which represents a change in the contact area with respect to a change in the contact force, by plotting the contact area with respect to the contact force at each measurement time point during a measurement time period; and may obtain the first feature values by using the created contact area change graph. In this case, the bio-information estimating apparatus may perform multi-dimensional equation curve fitting on the contact area change graph, and may perform differentiation on the graph obtained as a result of the fitting, to obtain a maximum slope, a minimum slope, an average slope of each of the unit sections, and the like as the first feature values.

In operation 640, the bio-information estimating apparatus may obtain contact pressure based on the contact force and the contact area. In this case, upon obtaining the contact pressure, the bio-information estimating apparatus may provide a user with guide information on an actual contact pressure value between the object and the sensor part, and may determine whether a contact state is normal based on the actual contact pressure value. Upon determining that the contact state is abnormal, the bio-information estimating apparatus may provide additional guide information for guiding a user to confirm a contact state.

In operation 650, the bio-information estimating apparatus may obtain second feature values based on the pulse wave signal and the contact pressure. For example, to estimate blood pressure using oscillometry, the bio-information estimating apparatus may obtain an oscillometric envelope, which represents contact pressure versus pulse wave by plotting a pulse wave amplitude based on a contact pressure value corresponding to each measurement time point, and may obtain the second feature values from the obtained oscillometric envelope. For example, the bio-information estimating apparatus may obtain, as the second feature value for estimating the MAP, a contact pressure value of a maximum amplitude point in the oscillometric envelope. Further, the bio-information estimating apparatus may obtain, as the second feature values for estimating the DBP and the SBP, contact pressure values of points each located to the left and right of the contact pressure value of the maximum amplitude point and having a predetermined ratio to the contact pressure value of the maximum amplitude point.

In operation 660, the bio-information estimating apparatus may estimate bio-information based on the first feature values and/or the second feature values. For example, upon obtaining the first feature values and the second feature values, the bio-information estimating apparatus may estimate blood pressure by applying a bio-information estimation model to the obtained values. Further, the bio-information estimating apparatus may estimate skin elasticity and/or skin age by using the first feature values. The bio-information estimating apparatus may estimate blood pressure, and skin elasticity and/or skin age at the same time, or may estimate nay one of these according to predetermined criteria.

In operation 670, the bio-information estimating apparatus may output an estimation result of bio-information. In this case, the bio-information estimating apparatus may output the estimating result of bio-information using various output devices, such as a display module for visual output, a speaker module for voice output, a haptic module for tactile output through vibration, tactile sensation, and the like.

Figure 7:
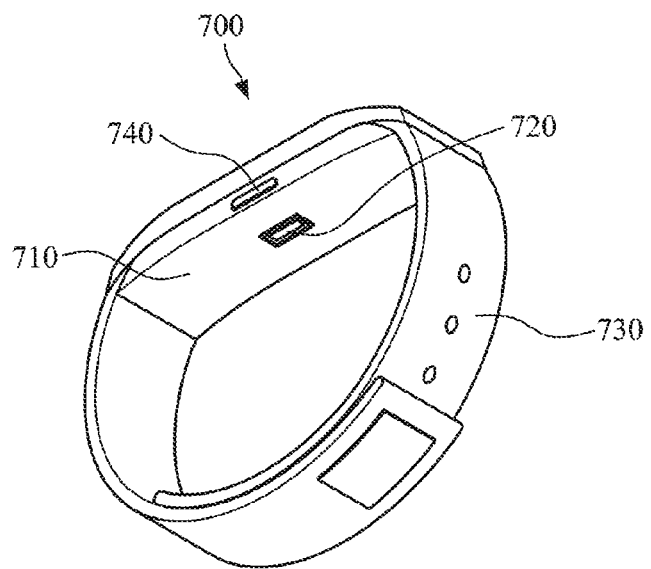
FIG. 7 is a diagram illustrating a wearable device, to which embodiments of a bio-information estimating appa-ratus are applied.

FIG. 7 is a diagram illustrating a wearable device, to which embodiments of a bio-information estimating apparatus are applied. Various embodiments of the above-described bio-information estimating apparatus may be mounted in a smart watch worn on a wrist or a smart band-type wearable device as illustrated herein. However, the wearable device is an example for convenience of explanation, and it may not be construed that application of the embodiments is limited to a smart watch or a smart band-type wearable device.

Referring to FIG. 7, a wearable device 700 includes a main body 710 and a strap 730.

The strap 730 may be flexible, and may be connected to both ends of the main body 710 to be bent around a user's wrist or may be bent in a manner that allows the strap 730 to be detached from a user's wrist. Alternatively, the strap 730 may be formed as a band that is not detachable. In this case, air may be injected into the strap 730 or an airbag may be included in the strap 730, so that the strap 730 may have elasticity according to a change in pressure applied to the wrist, and the change in pressure of the wrist may be transmitted to the main body 710.

A battery, which supplies power to the wearable device 700, may be embedded in the main body 710 or the strap 730.

Further, the main body 710 includes, on one side, a sensor part 720. The sensor part 720 may include: an area sensor for measuring a contact area between a wrist and the area sensor while the wrist touches the area sensor; a pulse wave sensor for measuring pulse wave signals from blood vessel tissues of the wrist while the wrist touches the area sensor; and a force sensor for measuring a contact force between the wrist and the area sensor. The pulse wave sensor may include one or more light sources for emitting light onto the wrist, and a detector for detecting light reflected or scattered from the blood vessel tissues. In this case, the light sources may emit light of different wavelengths, and may be disposed at different distances from the detector.

When a user changes contact pressure between the wrist and the sensor part 720 during a predetermined period of time to measure bio-information, the sensor part 720 may measure the pulse wave signal, the contact force, and the contact pressure. For example, a user may change contact pressure between the wrist and the sensor part 720 while wearing the main body 710 by touching a display, mounted on one surface of the main body 710, e.g., an opposite surface to the sensor part 720, with gradually increasing force with a finger of the other hand. Alternatively, a user may change a thickness of the wrist by making hand movements, e.g., slowly opening the hand after clenching the first while wearing the main body 710 on the wrist. In this case, the change in the thickness of the wrist leads to a change in tension of the strap wrapped around the wrist, thereby causing a change in contact pressure between the wrist and the sensor part 720.

Further, the main body 710 may include a processor that estimates bio-information based on information on the pulse wave signal, the contact force, the contact area, and the like, and controls various functions.

Upon receiving a request for estimating bio-information from a user, the processor may generate a control signal to control the sensor part 720. Once the contact force and the contact area are measured, the processor may obtain a first feature value based on the measured contact force and contact area. Further, the processor may obtain a contact pressure value based on the contact force and the contact area, and may obtain a second feature value by using the obtained contact pressure value and the pulse wave signal. The processor may estimate bio-information, e.g., blood pressure, by using the first feature value and the second feature value. In addition, the processor may estimate additional bio-information, e.g., skin elasticity and/or skin age, by using the first feature value, which is described above in detail.

Upon receiving the request for estimating bio-information from a user, the processor may provide the user with guide information on contact pressure through a display, so that the user may apply pressure to the main body 710 to change the contact pressure between the sensor part 720 and the object.

In this case, the display may be mounted on a front surface of the main body 710, and may visually output guide information on contact pressure and/or an estimation result of bio-information.

The storage may be mounted in the main body 710, and may store various types of information processed by the processor, and various criteria for estimating bio-information.

Further, the wearable device 700 may include a manipulator 740 that receives a control instruction of a user and transmits the received control instruction to the processor. The manipulator 740 may be mounted on a side surface of the main body 710, and may include an input interface (e.g., a physical hardware button) for performing a function for inputting a instruction to turn on/off the wearable device 700.

Moreover, the wearable device 700 may include a communication interface for transmitting and receiving various data to and from an external device, and various other modules for performing additional functions provided by the wearable device 700.

Figure 8:
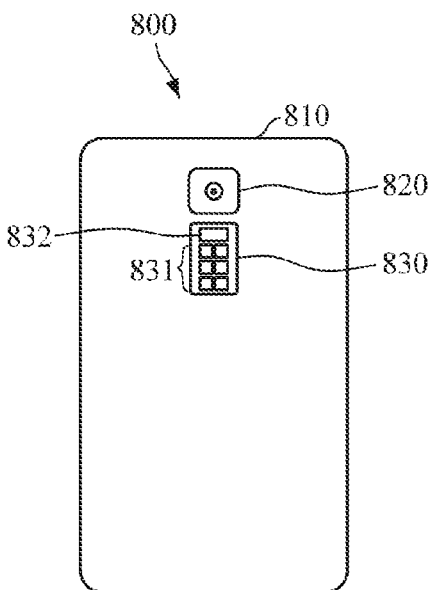
FIG. 8 is a diagram illustrating a smart device, to which embodiments of a bio-information estimating apparatus is applied.

FIG. 8 is a diagram illustrating a smart device, to which embodiments of a bio-information estimating apparatus is applied. In this case, the smart device may be a smartphone, a tablet PC, and the like.

Referring to FIG. 8, a smart device 800 includes a sensor part 830 mounted on one surface of a main body 810. In this case, the sensor part 830 may include a pulse wave sensor, which includes at least one or more light sources 831 and a detector 832, a force sensor, and an area sensor. As illustrated in FIG. 8, the sensor part 830 may be mounted on a rear surface of the main body 810, but is not limited thereto. Further, the sensor part 830 may be configured in combination with a fingerprint sensor or a touch panel mounted on a front surface. In this case, the fingerprint sensor or the touch panel may function as an area sensor, and a pulse wave sensor or a force sensor may be mounted at a lower portion of the fingerprint sensor or the touch panel.

In addition, a display may be mounted on a front surface of the main body 810. The display may visually display an estimation result of bio-information and the like. The display may include a touch panel, and may receive various types of information input through the touch panel and transmit the received information to the processor.

Moreover, an image sensor 820 may be mounted in the main body 810. When a user's finger approaches the sensor part 830 to measure a pulse wave signal, the image sensor 820 may capture an image of the finger and may transmit the captured image to the processor. In this case, based on the image of the finger, the processor may identify a relative position of the finger with respect to an actual position of the sensor 830, and may provide the relative position of the finger to the user through the display, so that pulse wave signals may be measured with improved accuracy.

Various other modules for performing many embodiments of the aforementioned bio-information estimating apparatus may be mounted in the smart device 800, and detailed description thereof will be omitted.

The embodiments can be realized as a computer-readable code written on a computer-readable recording medium. The computer-readable recording medium may be any type of recording device in which data is stored in a computer-readable manner.

Examples of the computer-readable recording medium include a ROM, a RAM, a CD-ROM, a magnetic tape, a floppy disc, an optical data storage, and a carrier wave (e.g., data transmission through the Internet). The computer-readable recording medium can be distributed over a plurality of computer systems connected to a network so that a computer-readable code is written thereto and executed therefrom in a decentralized manner. Functional programs, codes, and code segments needed for realizing the embodiments can be easily deduced by one of ordinary skill in the art.

Inventive concepts have been described herein with regard to embodiments. However, it will be obvious to those skilled in the art that various changes and modifications can be made without changing technical conception and features. Thus, it is clear that the above-described embodiments are illustrative in all aspects and are not intended to limit the disclosure.

What is claimed is:

1. A bio-information estimating apparatus comprising:
a main body;
a display mounted on a first surface of the main body;
a sensor part mounted on a second surface of the main body that is opposite to the first surface of the main body and configured to come into contact with a skin of a user, the sensor part comprising a pressure sensor and an area sensor, the pressure sensor configured to, based on an object contacting the pressure sensor, measure a contact force that is applied by the object to the pressure sensor, and the area sensor configured to measure a contact area of the object that is applied to the sensor part, the sensor part further comprising a pulse wave sensor that includes a light source that emits light onto the skin of the user and a complementary metal oxide semiconductor (CMOS) image sensor that detects the light emitted by the light source and scattered or reflected from the skin of the user;
a physical hardware button provided on the main body; and
a processor mounted on the first surface or second surface of the main body and electrically connected to the display and the sensor part, the processor configured to:
create, upon activation of the physical hardware button and using a signal from the pressure sensor and a signal form the area sensor, a contact area change graph representing a first change in the contact area with respect to a second change in the contact force, by plotting the contact area with respect to the contact force at each of measurement time points, and
obtain a first feature value, using the contact area change graph, based on the first change in the contact area with respect to the second change in the contact force,
estimate first bio-information, based on the first feature value, and
output the estimated first bio-information to the display, wherein the bio-information estimating apparatus is a wearable device.

2. The bio-information estimating apparatus of claim 1, wherein the first feature value comprises any one or any combination of a maximum slope, a minimum slope, and an average slope of each of predetermined unit sections of the contact area change graph.

3. The bio-information estimating apparatus of claim 1, wherein the first bio-information comprises either one or both of skin elasticity and skin age.

4. The bio-information estimating apparatus of claim 3, wherein as a change trend of the first feature value increases in comparison to a reference feature value that is obtained from the user at a reference time, the skin elasticity decreases, and the skin age increases, and wherein as the change trend of the first feature value decreases compared to the reference feature value, the skin elasticity increases, and the skin age decreases.

5. The bio-information estimating apparatus of claim 3, wherein the processor is further configured to estimate either one or both of the skin elasticity and the skin age by applying a pre-defined bio-information estimation model to a change trend of the first feature value in comparison with a plurality of feature values that is obtained from a plurality of subjects.

6. The bio-information estimating apparatus of claim 1, wherein the sensor part is further configured to measure a pulse wave signal, and wherein the processor is further configured to obtain a second feature value, based on the pulse wave signal, and estimate second bio-information, based on the first feature value and the second feature value.

7. The bio-information estimating apparatus of claim 6, wherein the second bio-information comprises a blood pressure, and the processor is further configured to obtain an oscillometry of the pulse wave signal, and obtain the second feature value, based on the oscillometry.

8. The bio-information estimating apparatus of claim 6, further comprising an output interface configured to output an estimation result of the first bio-information and the second bio-information.

9. The bio-information estimating apparatus of claim 6, further comprising a communication interface configured to transmit an estimation result of the first bio-information and the second bio-information, to an external device.

* * * * *